(12) United States Patent
George et al.

(10) Patent No.: US 6,592,882 B2
(45) Date of Patent: *Jul. 15, 2003

(54) COSMETIC COMPOSITIONS CONTAINING FLUORESCENT MINERALS

(75) Inventors: Liliana George, Centerport, NY (US); Joseph Gubernick, New York, NY (US); Gheorghe Cioca, Lake Grove, NY (US); Andrew J. Bevacqua, E. Setauket, NY (US)

(73) Assignee: Color Access, Inc., Melville, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/320,602

(22) Filed: May 26, 1999

(65) Prior Publication Data

US 2002/0012681 A1 Jan. 31, 2002

(51) Int. Cl.$^7$ .......................... A61K 7/00; A61K 7/021
(52) U.S. Cl. .......................... 424/401; 424/63; 424/400
(58) Field of Search .................................. 424/401, 63

(56) References Cited

U.S. PATENT DOCUMENTS

| 4,857,306 A | 8/1989 | Roller .......................... 424/63 |
| 5,635,109 A | 6/1997 | Otsuka ................. 252/301.4 P |
| 5,755,998 A | 5/1998 | Yamazaki et al. .... 252/301.4 P |
| 5,830,446 A | 11/1998 | Berthiaume et al. ....... 424/70.1 |

FOREIGN PATENT DOCUMENTS

| BR | 95 05394 | 10/1997 |
| EP | 0 370 470 | 5/1990 |
| EP | 0 542 669 | 5/1993 |
| FR | 1458223 | 1/1967 |
| JP | 62 273907 | 11/1987 |
| JP | 2060978 | 3/1990 |
| JP | 3250075 | 11/1991 |
| JP | 10 120520 | 5/1998 |
| JP | 10 330209 | 12/1998 |
| JP | 10 330239 | 12/1998 |

OTHER PUBLICATIONS

Michael J. Fellner, M.D., "Green Autofluorescence in Human Epidermal Cells" Arch Dermatol—vol. 112, pp. 667–670, (May 1976).

Haishan Zeng, et al., "Spectroscopic and Microscopic Characteristics of Human Skin Autofluorescence Emission", Photochemistry and Photobiology: vol. 61, No. 6, pp. 639–645, (1995).

David J. Leffell, M.D., et al., "In Vivo Fluorescence of Human Skin: A Potential Marker of Photoaging", Arch Dermatol—vol. 124, pp. 1514–1518 (Oct. 1988).

International Cosmetic Ingredient Dictionary and Handbook, 7th Edition 1997, vol. 2, Published by The Cosmetic Toiletry, and Fragrance Association, Editors John A. Wenninger, et al., CTFA, pp. 1628–1630, and copy of book cover.

*Primary Examiner*—Shelley A. Dodson
(74) *Attorney, Agent, or Firm*—Karen A. Lowney, Esq.

(57) ABSTRACT

The invention relates to cosmetic composition comprising a fluorescent-effective amount of at least one fluorescent mineral powder, in combination with a cosmetically acceptable vehicle, wherein the powder, when the composition is applied, does not substantially alter the color of the skin. The compositions of the invention can be used as color cosmetics and skin treatment products, to replenish the skin's natural fluorescent glow.

28 Claims, No Drawings

US 6,592,882 B2

COSMETIC COMPOSITIONS CONTAINING FLUORESCENT MINERALS

FIELD OF THE INVENTION

The invention relates to cosmetic compositions and methods. More specifically, the invention relates to compositions and methods that replenish the skin's natural fluorescence.

BACKGROUND OF THE INVENTION

It has long been recognized that normal skin exhibits a substantial level of fluorescence (Fellner, Arch. Dermatol. 112: 667–670, 1976). The fluorescence apparently exists throughout the different layers of the skin, with the epidermis showing the weakest levels, the stratum corneum being slightly stronger, and the most intense emissions being found in the dermis and subcutaneous fat (Zeng, et al., Photochem. Photobiol. 61: 639–645, 1995). The level of epidermal fluorescence varies depending upon the color of the individual's skin, with darker skins showing a higher level of fluorescence than lighter skins. However, the fluorescence in the dermis is apparently related to elements common to all skin types: elastin and collagen. The spectra of living human skin is measurable over a wide excitation wavelength, with green being the dominant autofluorescence color.

With particular respect to the dermis, it well-known that the elements responsible for fluorescence are susceptible to substantial alteration in quality and quantity due to advancing age as well as UV exposure. It is widely accepted that these changes in elastin and collagen are at least partially, and probably predominantly, responsible for many of the external changes characteristic of aged skin, whether chrono- or photoaged. The external changes that are immediately identifiable as being associated with loss or alteration of these fibers include the readily defined features, such as lines, wrinkles, and skin atrophy; however, another common age-associated feature that is perhaps more difficult to characterize is familiar loss of luster, color and tone of mature or photodamaged skin.

Interestingly, the change in structure of collagen and elastin observed at least with respect to photoaging has been shown to be correlated with a decline in the intensity of fluorescence in the photoaged skin.(Leffell, et al. Arch. Dermatol. 124: 1514–1518, 1988). This change is also reflected in chronoaged skin, which in middle age begins to lose its green fluorescence, and in later years, loses its blue fluorescence. It is very likely that the decline in the vigorous "glow" common to young, healthy skin is related at least in part to the this observed loss of fluorescence. Nonetheless, cosmetics and skin care products have traditionally focused on the camouflaging of the most easily characterized signs of aging, such as wrinkles; there has been little effort to develop products which address the seemingly more intangible problem of renewing the glow of youth in the more mature individual's skin. The present invention now provides a solution to this problem.

SUMMARY OF THE INVENTION

The present invention relates to cosmetic compositions comprising effective amounts of at least one fluorescent mineral powder, in combination with a cosmetically acceptable vehicle. The compositions, when applied to the skin, replenish the fluorescence that may have been lost due to chrono- or photoaging, while not necessarily providing a substantial amount of color on the skin. The invention also relates to a method of imparting a glow to the skin comprising applying to the skin a cosmetic composition comprising an effective amount of a fluorescent mineral powder. The compositions can also be used to reduce the appearance of dark circles and lines on the skin, as well as reduce the appearance of symptoms of chrono- and photoaging.

DETAILED DESCRIPTION OF THE INVENTION

The use of fluorescent materials in cosmetics is not unknown. There are a number of reported uses of fluorescent pigments or dyes in cosmetics, particularly in color cosmetics, principally to impart an additional dimension to the color (see, e.g., EP 370470, JP 2060978, JP 3250075, and EP 542669). In each of these cases, a fluorescent dye or pigment, such as D&C Orange No. 5, or ultramarine blue, typically constitutes the sole or primary colorant component of the cosmetic, and the color of the dye is visually prominent in the product. Similarly, precious gemstone powders have also been suggested for use in color cosmetic products, as disclosed in U.S. Pat. No. 4,857,306; however, no reference is made to fluorescence in the gemstones, and again, the gemstones constitute the sole or primary color of the composition.

In contrast to the prior art, the present invention utilizes fluorescent mineral powders in such a way as to confer a fluorescent glow to both the composition and to the skin when applied but does not necessarily confer any visually distinct color to the skin. Fluorescent minerals are naturally occurring materials, and have the advantage over chemical fluorescent dyes in this regard, as well as being substantially non-irritating. Also unlike many prior art uses of fluorescent dyes, the powder will not constitute a primary color component of the composition as it appears on the skin, and in certain embodiments, particularly in the case in which the mineral is used in a non-color cosmetic, it will not confer any color change to the skin that is appreciable to the naked eye. The fluorescent mineral powders can be used in a color-conferring cosmetic, and a strongly fluorescent mineral can contribute to the intensity of the primary color in such a composition; the fluorescent minerals can also be used in a non-color cosmetic, e.g., a skin care or transparent or translucent cosmetic which is intended to confer little or no color to the skin after application. The term "effective amount" as used in the specification and claims is that amount of any fluorescent mineral powder that will confer an observable fluorescence to the composition in which it is placed.

Any fluorescent mineral may be employed in the compositions of the invention. The minerals can be conveniently grouped according to the color of the dominant fluorescence produced by the minerals, although there is some gradation in the spectrum of fluorescence, and some minerals may fluoresce differently depending on their exact composition and/or impurities contained therein. In one embodiment, the mineral produces a green to bluish green fluorescence; minerals of this type include, but are not limited to, andalusite and chiastolite (aluminum silicate); amblygonite (basic lithium aluminum phosphorate); phenakite (beryllium silicate); variscite (hydrous aluminum phosphate); serpentine (basic magnesium silicate); amazonite (potassium aluminum silicate); amethyst (silicon dioxide); chrysoberyl (beryllium aluminum oxide); turquoise (copper-containing basic aluminum phosphate); colorless, yellow or pink tourmaline (borosilicate); amber (succinite/various resins); opal (hydrous silicon dioxide); cerussite (lead carbonate); fuchsite (potassium aluminum silicate); diopside (calcium magnesium silicate); ulexite (hydrous sodium calcium borate); aragonite (calcium carbonate); and willemite (zinc silicate). Particularly preferred among these are the silicates, particularly those with a strong fluorescence, such as fuchsite, diopside, ulexite, aragonite and willemite. In another embodiment, the mineral emits a blue fluorescence; examples of such minerals include dumortierite (aluminum borate silicate); scheelite (calcium tungstate); smithsonite (zinc carbonate); danburite (calcium boric silicate); benitoite (barium titanium silicate); fluorite (fluorospar); and halite. Other fluorescence categories include red or orange, as represented, for example in axinite (calcium aluminum borate silicate); scapolite (sodium calcium aluminum silicate); kyanite (aluminum silicate); sphalerite (zinc sulphite); calcite (calcium carbonate); petalite (lithium aluminum silicate); or yellow, as represented by apatite (basic fluoro- and chloro-calcium phosphate) or cerussite (lead carbonate). In one preferred embodiment, the mineral is selected from those emitting blue or green fluorescence, or combinations thereof, so as to directly mimic the skin's natural fluorescent color. However, in another embodiment, the mineral's fluorescent color can be any one or a combination of colors, the selection being made for the purpose of enhancing, complementing, or counteracting a given skin tone color.

The powders of the invention are prepared by standard grinding techniques, such as jet milling, roller milling or pulverization. The average particle size of the powders will normally be, for aesthetic reasons, no larger than about 45$\mu$; preferably the particle size is between 0.5–20$\mu$, and more preferably between about 0.5 and 5$\mu$, with the harder minerals preferably being ground within the lower end of the recommended range. The amounts of the powders may be varied depending upon the intensity of the fluorescence and color of the mineral, and can be present in an amount of from about 0.01% to about 50%, more preferably, however, the amount used will be between about 0.01% up to about 10%, most preferably about 1% to about 8%, with about 2–5% being the most commonly employed amount.

It may also be desirable to treat the powders to render them more hydrophobic, as the powders normally have a high affinity for binding water. As with more traditional pigments, the powders can be coated with a hydrophobic coating such as metal salts of fatty acids, e.g., magnesium stearate, magnesium myristate, or aluminum stearate.

The powders can be incorporated into any kind of vehicle that is normally used for cosmetic compositions. For example, the minerals can be added to solutions, colloidal dispersions, emulsions (oil-in-water or water-in-oil), suspensions, powders, creams, lotions, gels, foams, mousses, sprays and the like. Methodology for formulation of different vehicle types is well known in the art, and can be found for example in Remington's The Science and Practice of Pharmacy, 19th Edition, Volume II. In one embodiment, the mineral powders are used in a powder color cosmetic, such as a face powder, an eye shadow, a blush. In another embodiment, the powders can be used as part of a liquid cosmetic, such as a liquid foundation, eyeliner, concealer or blush. In addition, the mineral powders can be used in solid or semi-solid gel or stick products, such as lipsticks, lip glosses, cream lipsticks, lip or eye pencils, stick foundations, concealers or stick blushes. A particularly preferred use is in a facial product, such as a foundation, concealer, or blush, the use of which will permit the most advantageous and recognizable replenishment of the skin's natural luster.

In the case of the use of the mineral powders in a color cosmetic, the powder preferably does not constitute the sole or even the primary colorant for the product. In a color cosmetic, the powder will be typically combined with other pigments or dyes. The additional color components can be either organic or inorganic. Examples of useful inorganic pigments include iron oxides (yellow, red, brown or black), ferric ammonium ferrocyanide (blue), manganese violet, ultramarine blue, chrome oxide (green), talc, lecithin modified talc, zeolite, kaolin, lecithin modified kaolin, titanium dioxide (white) and mixtures thereof. Other useful pigments are pearlants such as mica, bismuth oxychloride and treated micas, such as titanated micas and lecithin modified micas.

The organic pigments include natural colorants and synthetic monomeric and polymeric colorants. Exemplary are phthalocyanine blue and green pigment, diarylide yellow and orange pigments, and azo-type red and yellow pigments such as toluidine red, litho red, naphthol red and brown pigments. Also useful are lakes, which are pigments formed by the precipitation and absorption of organic dyes on an insoluble base, such as alumina, barium, or calcium hydrates. Polymeric colorants include nylon powder, polyethylene, and polyesters. The polyesters can include linear, thermoplastic, crystalline or amorphous materials produced using one or more diols and one or more dicarboxylic acids copolymerized with colorants. An exemplary list of cosmetically acceptable colorants can be found in the International Cosmetic Ingredient Dictionary and Handbook, 7th Edition, CTFA, 1997, pp. 1628–1630, the contents of which are incorporated herein by reference. In the color cosmetics of the present invention, colorants other than the fluorescent powder can constitute from about 1–99% by weight of the final product, the amount depending upon the intended use and the strength of color desired.

In an alternate embodiment, the mineral powders are employed in a non-color cosmetic, such as a transparent or translucent product, or a skin treatment product. When used in a skin treatment product, the powders can be used alone as the primary component, for the purpose of evening or brightening skin tone, to disguise dark shadows, undereye circles, lines and wrinkles on the skin, or to counteract the effects of rosacea. Alternately, they can be used in a product combined with additional skin care treatment actives, such as those that improve or eradicate age spots, keratoses and wrinkles, analgesics, anesthetics, anti-acne agents, antibacterials, antiyeast agents, antifungal agents, antiviral agents, antidandruff agents, antidermatitis agents, antipruritic agents, antiemetics, antimotion sickness agents, anti-inflammatory agents, antihyperkeratolytic agents, anti-dry skin agents, antiperspirants, antipsoriatic agents, antiseborrheic agents, antiaging agents, antiwrinkle agents, antiasthmatic agents and bronchodilators, sunscreen agents, antihistamine agents, skin lightening agents, depigmenting agents, wound-healing agents, vitamins, corticosteroids, self-tanning agents, or hormones. The amount of active agent to be used in any given formulation is readily determined in accordance with its usual dosage. In this specific application, in which color is not a focus of the product, the mineral powders are normally used in an amount of from about 0.01 to about 10% by weight of the product.

The mode of application of the compositions of the invention will depend upon the final intended use. In a color cosmetic/makeup product, the powder-containing composition will normally be applied on an as-needed basis, as part of the user's daily makeup routine, particularly to the face. As a treatment product, the composition can be applied daily, with or without makeup, simply to replenish the facial or other skin's natural glow and to cause unadorned skin to appear healthier and younger. It may also be applied to particular trouble spots, such as dark undereye shadows, in order to brighten their appearance. Although the amount of product applied will also vary depending upon the final end use, and the appearance intended to be achieved, as a guideline, to achieve an optimum glow, the product will normally be applied in an amount of about 0.1 $\mu g/cm^2$ to 2 $mg/cm^2$ of skin.

The invention is further illustrated by the following non-limiting examples.

EXAMPLES

Example I

This example illustrates the preparation of a non-color formulation to be used to replenish the green fluorescence of the skin. Amethyst has a greenish fluorescence.

| Material | Weight Percent |
| --- | --- |
| deionized water | QS |
| methyl paraben | 0.01 |
| ceteth-20 | 2.50 |
| disodium EDTA | 0.10 |
| BTC (50% solution) | 0.20 |
| whey protein | 0.70 |
| amethyst powder | 2.00 |
| Vitamin E | 0.10 |
| dimethicone (100 cs) | 1.50 |
| cyclomethicone | 4.50 |
| polyacrylamide | 3.00 |

The first two components are added to an emulsification vessel and heated to 75° C. EDTA and BTC are also premixed, as are dimethicone and cyclomethicone. The remaining components of the formula are added to the vessel, and mixed until all solids are completely dissolved or dispersed. The premixed components are then added and mixed to homogeneity. The polyacrylamide is mixed in last, and the composition is then cooled.

Example II

This example illustrates the preparation of a color cosmetic, specifically a concealer, using two fluorescent minerals, diopside and calcite. Diopside fluoresces violet, yellow, orange and green, and itself provides a taupe color to the composition. Calcite fluoresces red, pink and orange, and provides a peach color to the composition.

| Material | Weight Percent |
| --- | --- |
| Deionized water | QS |
| Polysorbate 85 | 0.50 |
| talc | 0.005 |
| titanium dioxide | 11.00 |
| diopside | 5.00 |
| cosmetic yellow | 1.00 |
| pure oxy red | 0.20 |
| pure oxy umber | 1.35 |
| propylene glycol | 12.00 |
| xanthan gum | 0.10 |
| magnesium aluminum silicate | 1.23 |
| lecithin | 1.00 |
| methyl paraben | 0.30 |
| triethanolamine | 1.50 |

-continued

| Material | Weight Percent |
| --- | --- |
| calcite | 3.00 |
| polydecene | 4.50 |
| caprylic/capric triglyceride | 3.50 |
| propylene glycol stearate | 3.00 |
| stearic acid | 3.20 |
| cetyl ester wax | 1.00 |
| propyl paraben | 0.10 |
| butyl paraben | 0.10 |
| cetyl alcohol | 0.10 |
| stearyl alcohol | 0.10 |

The first 15 items are combined together as the water phase, the remaining items are combined as the oil phase. The oil phase is added to the water phase at 85° C., and agitation continued while cooling, to produce an oil-in-water emulsion. The colors of the added minerals are not observable in the final composition.

Example III

This example illustrates the preparation of a compact foundation, using two fluorescent minerals, for the benefits of replenishing the skin's glow and to provide an even skin tone by using yellow fluorescence to counteract redness. The mineral apatite fluoresces yellow (as well as purple to pink), and fuchsite fluoresces green. The minerals are jet milled and used in the following formula:

| Material | Weight Percent |
| --- | --- |
| Propylene glycol dicaprylate/dicaprate | 20.00 |
| coco-caprylate/caprate | 16.00 |
| dimethicone/polysilicone | 12.00 |
| nylon-12 | 10.00 |
| apatite | 6.00 |
| barium sulfate | 2.00 |
| mica/magnesium myristate | 6.50 |
| titanium dioxide/magnesium myristate | 2.00 |
| fuchsite/magnesium myristate | 8.00 |
| yellow iron oxide/magnesium myristate | 1.25 |
| red iron oxide/magnesium myristate | 0.45 |
| black iron oxide/magnesium myristate | 0.30 |
| polyethylene | 8.00 |
| BHT | 0.03 |
| propyl paraben | 0.10 |
| butyl paraben | 0.10 |
| carnauba wax | 5.27 |
| tribehenin | 2.00 |

The first 12 ingredients are premixed and passed through a ball mill. The polyethylene is added to the main kettle and heated to 100–105° C.; when melting is completed, premixed ingredients 1–12 are added, the temperature adjusted to 90–95° C., and mixed until uniform. The last 4 ingredients are also premixed, and then added over the phase in the main kettle, mixed in until uniform, and then cooling of the mixture is started.

What is claimed is:

1. A color cosmetic composition for application to the skin comprising a fluorescent-effective amount of a fluorescent mineral powder, in combination with a cosmetically acceptable vehicle and at least one colorant iron oxide, titanium dioxide or a combination thereof, wherein the powder, when the composition is applied, does not constitute a primary source of the color on the skin.

2. The composition of claim 1 in which the mineral shows a green or blue fluorescence.

3. The composition of claim 1 in which the mineral powder has an average particle size of no greater than about 45μ.

4. The composition of claim 1 in which the particle size is from about 0.5 to about 5μ.

5. A cosmetic composition for application to skin comprising a fluorescent-effective amount of at least one fluorescent mineral powder, in combination with a cosmetically acceptable vehicle, wherein the powder, when the composition is applied, does not constitute a primary source of color on the skin, in which the mineral is selected from the group consisting of dumortierite, scheelite, smithsonite, danburite, benitoite, fluorite, and halite.

6. A cosmetic composition for application to skin comprising a fluorescent-effective amount of at least one fluorescent mineral powder, in combination with a cosmetically acceptable vehicle, wherein the powder, when the composition is applied, does not constitute a primary source of color on the skin, in which the mineral is selected from the group consisting of axinite, scapolite, kyanite, sphalente, calcite, petalite, apatite, and cerussite.

7. The composition of claim 5 which is a non-color cosmetic.

8. The composition of claim 5 in which the mineral powder provides substantially no color when applied on the skin.

9. The composition of claim 1, in which the mineral is selected from the group consisting of andalusite, chiastolite, amblygonite, phenakite, variscite, serpentine, amozonite, amethyst, chrysoberyl, turquoise, colorless tourmaline, yellow tourmaline, pink tourmaline, amber, opal, cerussite, fuchsite, disopide, ulexite, aragonite, and willemite.

10. A color cosmetic composition for application to skin comprising a fluorescent-effective amount of a fluorescent mineral powder, in combination with a cosmetically acceptable vehicle and at least one colorant selected from the group consisting of inorganic pigments, natural colorants, synthetic organic monomeric colorants, synthetic organic polymeric colorants, and combinations thereof, wherein the powder, when the composition is applied, does not constitute a primary source of color on the skin, in which the mineral is selected from the group consisting of fuchsite, diopside, ulexite, aragonite and willemite.

11. A color cosmetic composition for application to skin comprising a fluorescent-effective amount of a fluorescent mineral powder, in combination with a cosmetically acceptable vehicle and at least one colorant selected from the group consisting of inorganic pigments, natural colorants, synthetic organic monomeric colorants, synthetic organic polymeric colorants, and combinations thereof, wherein the powder, when the composition is applied, does not constitute a primary source of color on the skin, in which the mineral is selected from the group consisting of dumortierite, scheelite, smithsonite, danburite, benitoite, fluorite, and halite.

12. A color cosmetic composition for application to skin comprising a fluorescent-effective amount of a fluorescent mineral powder, in combination with a cosmetically acceptable vehicle and at least one colorant selected from the group consisting of inorganic pigments, natural colorants, synthetic organic monomeric colorants, synthetic organic polymeric colorants, and combinations thereof, wherein the powder, when the composition is applied, does not constitute a primary source of color on the skin, in which the mineral is selected from the group consisting of axinite, scapolite, kyanite, sphalerite, calcite, petalite, apatite, and cerussite.

13. The composition of claim in which the powder is hydrophobically treated.

14. The composition of claim 1 which is a foundation, eye shadow, or blush.

15. A method of providing a glow to the skin which comprises applying to the skin a composition according to claim 1.

16. A method of providing a glow to the skin which comprises applying to the skin a composition according to claim 10.

17. A method of providing a glow to the skin which comprises applying to the skin a composition according to claim 11.

18. The composition of claim 6 which is a non-color cosmetic.

19. The composition of claim 6 in which the mineral powder provides substantially no color when applied on the skin.

20. The composition of claim 5 in which the mineral powder has an average particle size of no greater than about 45μ.

21. The composition of claim 5 in which the particle size is from about 0.5 to about 5μ.

22. The composition of claim 6 in which the mineral powder has an average particle size of greater than about 45μ.

23. The composition of claim 6 which the particle size is from about 0.5 to about 5μ.

24. A method for providing, a glow to the skin which comprises applying to the skin a composition according to claim 5.

25. A method for providing a glow to the skin which comprises applying to the skin a composition according to claim 6.

26. A method for providing a glow to the skin which comprises applying to the skin a composition according to claim 9.

27. A method for providing a glow to the skin which comprises applying to the skin a composition according to claim 12.

28. A method for providing a glow to the skin which comprises applying to the skin a composition according to claim 13.

* * * * *